United States Patent [19]

Longoria

[11] Patent Number: 5,081,017
[45] Date of Patent: Jan. 14, 1992

[54] METHOD AND APPARATUS FOR DETECTION AND QUANTITATION OF BACTERIA

[75] Inventor: Claude C. Longoria, Sugar Land, Tex.

[73] Assignee: Texas BioResource Corporation, Stafford, Tex.

[21] Appl. No.: 427,920

[22] Filed: Oct. 25, 1989

Related U.S. Application Data

[63] Continuation of Ser. No. 830,182, Feb. 18, 1986, abandoned.

[51] Int. Cl.⁵ .......................... C12Q 1/24; C12M 1/34
[52] U.S. Cl. ............................................ 435/30; 435/5; 435/29; 435/34; 435/39; 435/173; 435/287; 435/311; 422/101; 424/3; 424/7.1; 210/474; 210/477; 210/455; 210/505
[58] Field of Search ............... 435/5, 29, 30, 34, 39, 435/173, 287, 311; 422/101; 210/474, 477, 455, 505; 424/3, 7.1

[56] References Cited

U.S. PATENT DOCUMENTS

| | | | |
|---|---|---|---|
| 3,482,943 | 12/1969 | Csizmas et al. | 435/34 X |
| 4,181,500 | 1/1980 | Cowsar et al. | 436/99 |
| 4,225,669 | 9/1980 | Melnick et al. | 435/39 X |
| 4,317,726 | 3/1982 | Shopel | 422/101 X |
| 4,336,337 | 6/1982 | Wallis et al. | 435/34 X |
| 4,477,575 | 10/1984 | Vogel et al. | 422/56 X |
| 4,614,585 | 9/1986 | Mehra et al. | 210/455 X |
| 4,623,461 | 11/1986 | Hossom et al. | 422/101 X |
| 4,632,901 | 12/1986 | Valkirs et al. | 436/807 X |
| 4,948,726 | 8/1990 | Longoria | 435/7 |

Primary Examiner—Robert A. Wax
Assistant Examiner—Ardin H. Marschel
Attorney, Agent, or Firm—James L. Jackson

[57] ABSTRACT

A bacterial staining composition, process and apparatus for detection and quantitation of gram negative and gram positive bacteria in fluid samples are disclosed. The composition comprises a net negatively charged filter onto which bacteria are adsorbed and concentrated, an acid diluent which alters the electrostatic charge of the bacteria, thus enabling adsorption of the bacteria to the filter, a bacterial stain operative at about pH 8 to 12, and a washing reagent which enhances the diffusion of free dye away from the immobilized, stained bacterial. The color intensity at the center of the filter surface manifests the stained bacteria. It is compared to a standard color guide to determine the number of bacterial present in the fluid sample.

25 Claims, 2 Drawing Sheets

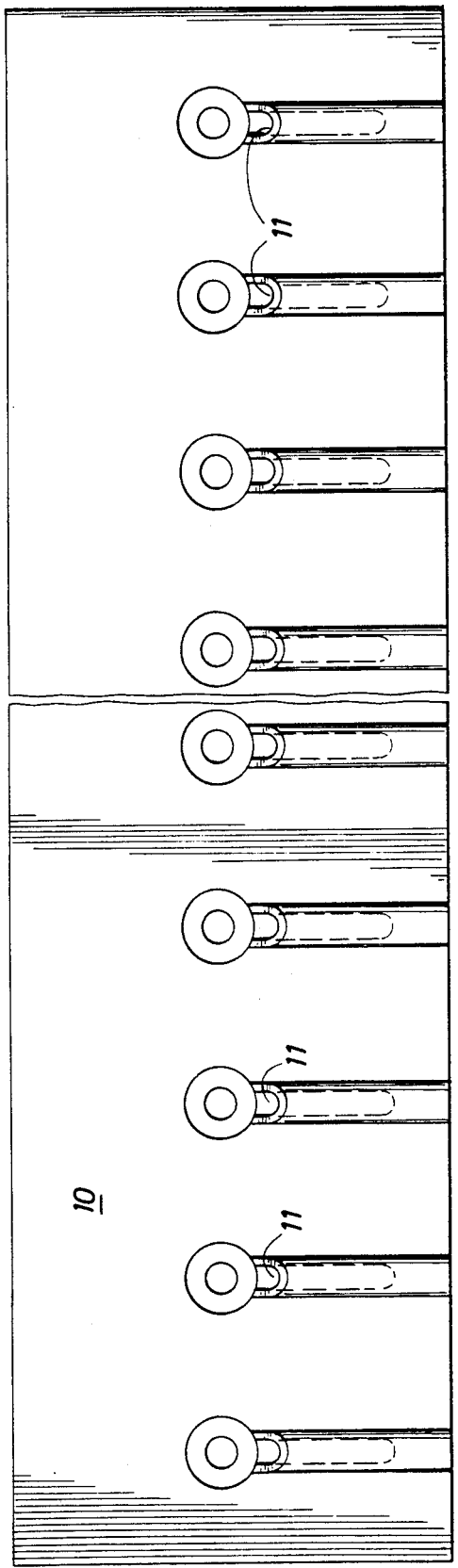
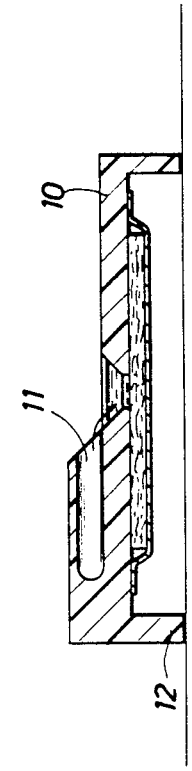
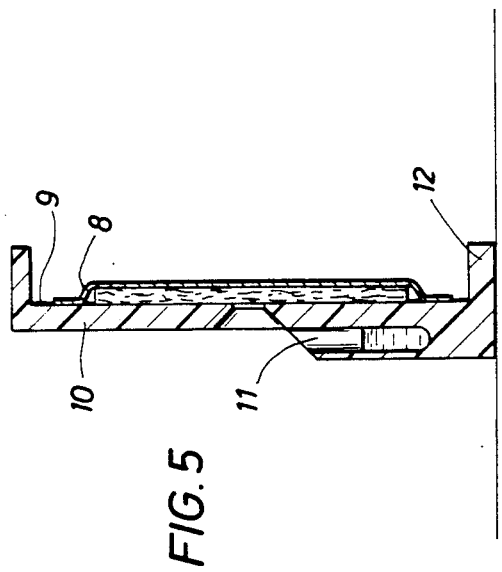

METHOD AND APPARATUS FOR DETECTION AND QUANTITATION OF BACTERIA

This is a continuation of prior complete application Ser. No. 06/830,182, filed on Feb. 18, 1986, by Claude C. Longoria, now abandoned.

FIELD OF THE INVENTION

This invention relates generally to testing procedures for bacteria in fluid samples such as human body fluids and more particularly to a method and apparatus for efficient, less cost, rapid testing procedures for identifying the presence and concentration of gram negative and gram positive bacteria strains in fluid samples.

BACKGROUND OF THE INVENTION

A need exists for a method to rapidly detect bacteria in urine and various other fluid samples.

Urine specimens are the major work load of the diagnostic laboratory. The most common urological disease is urinary-tract infections in children, pregnant women, diabetics and geriatric patients, (bacteriuria). In hospitals, bacteriuria is the predominant form of nosocomial infection. In view of the frequent asymptomatic urinary-tract infections bacteriuria tests must be sufficiently simple and economical to permit routine testing. A need, therefore, exists for simple, rapid, inexpensive screening tests to facilitate diagnosis and ensure prompt treatment of bacteriuric patients.

The conventional method for detection of urinary-tract infections is by inoculation of urine onto agar culture plates and incubation of these plates at optimal temperatures (usually 37 degrees C.) for 24-48 hours; bacteria are detected by formation of colonies on the agar surface. Fastidious bacteria may not grow on conventional culture media, and a variety of agar media may be required to detect these bacteria. This procedure is time consuming and expensive.

Although staining techniques, such as the Gram Stain Method, are known in clinical microbiology light microscopy is required, and the procedures are time consuming and require a skilled microbiologist. Other prior art processes involve staining of bacteria followed by concentration by centrifugation or filtration. These processes require chelating agents and positively-charged small pore filters, and suffer clogging and interference from anionic pigments, blood and other substances which may be present in urine.

It has now been unexpectedly discovered that both gram negative and gram positive bacteria can be stained for simple, rapid detection by means of the composition of the present invention. Concentrated bacteria stained with the composition described herein are readily visible and can thus be rapidly detected without resorting to light microscopic examination by specially trained personnel, or the use of expensive, perishable agar cultures. The present invention allows the efficient detection of bacteria while reducing clogging and pigment interference common to prior art methods. Furthermore, it was discovered through tests that inexpensive, simple, and rapid quantitative analysis of bacteria is possible employing the present staining composition.

SUMMARY OF THE INVENTION

A composition for staining both gram negative and gram positive bacteria is provided. The composition comprises an inorganic acid diluent, a dye soluble at a pH of 8 to 12 which preferentially stains bacteria, a washing reagent composed of an inorganic acid, and a filter paper or glass filter of a net negative charge. Bacteria are electrostatically immobilized and concentrated on the filter and are stained with the dye solution. The free dye is then removed with the washing reagent. The bacteria, which retain the dye, become visible and thus may be detected and quantitated by comparing the color intensity of the filter surface (due to the stained bacteria) to a nomograph or other calibrated standard based on color intensities obtained using known amounts of bacteria. The total test time is usually less than one minute.

It is therefore a primary feature of the present invention to provide a novel method and apparatus for rapid detection and quantitation of bacteria to thus enable rapid initiation of treatment of patients for bacterial infections.

It is also a feature of this invention to provide novel method and apparatus for bacteria detection wherein a number of tests may be conducted simultaneously for detection and quantitation of bacteria to thus minimize the time period for detection of bacteria that might be present in samples of body fluid.

It is another feature of this invention to provide novel method and apparatus for identifying the presence and concentrations of both gram negative and gram positive bacteria strains in fluid samples.

Among the several features of this invention is contemplated the provision of a novel method and apparatus for bacteria detection through employment of a dye for staining of the bacteria together with a filter composed of paper, glass, or any other suitable material having a net negative charge for electrostatically immobilizing and concentrating the bacteria on the filter prior to staining.

It is another feature of this invention to provide a novel method and apparatus for quantifying the concentration of bacteria in a fluid sample by means of visible comparison of the color intensity of stained bacteria on the filter surface with a nomograph or other calibrated standard based on color intensities obtained using known concentrations of bacteria.

BRIEF DESCRIPTION OF THE DRAWINGS

So that the manner in which the above recited features, advantages and objects of the present invention are attained and can be understood in detail, more particular description of the invention, briefly summarized above, may be had by reference to the embodiments thereof which are illustrated in the appended drawings.

It is to be noted, however, that the appended drawings illustrate only typical embodiments of this invention and are therefore not to be considered limiting of its scope, for the invention may admit to other equally effective embodiments.

Figure 1:
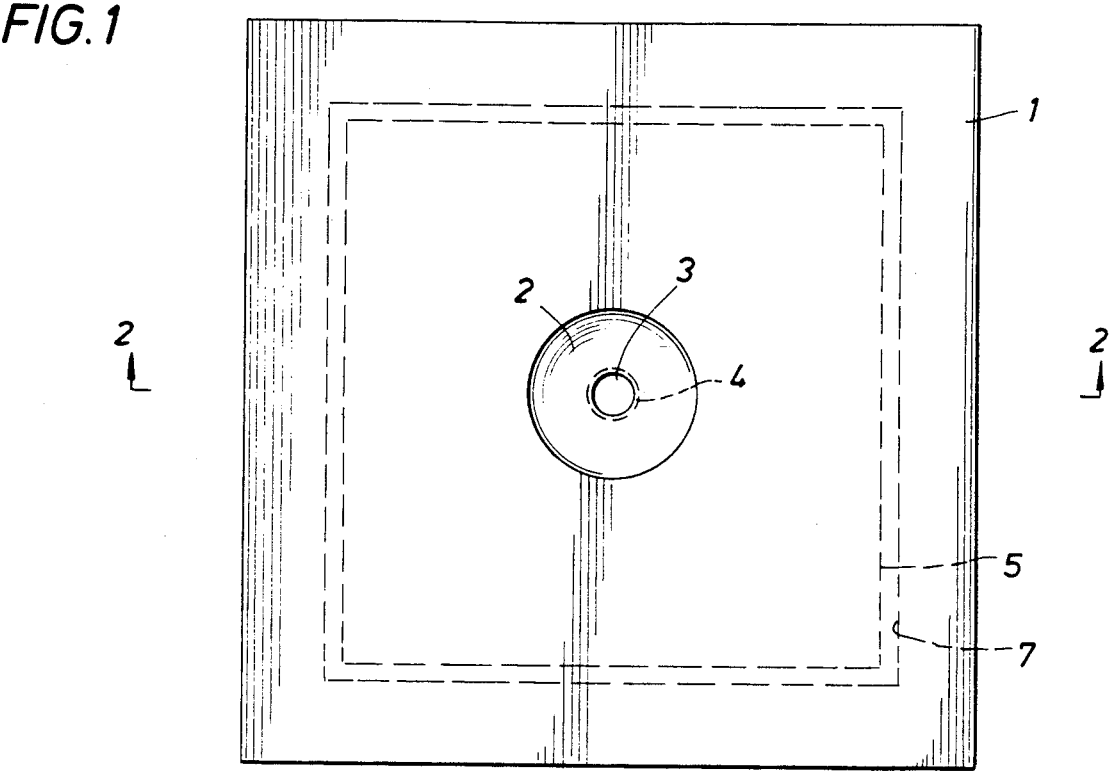

Preferred embodiments of this invention have been chosen for purposes of illustration and description and are shown in the accompanying drawings forming a part of this specification wherein:

FIG. 1 is a plan view of filter apparatus constructed in accordance with the present invention.

Figure 2:
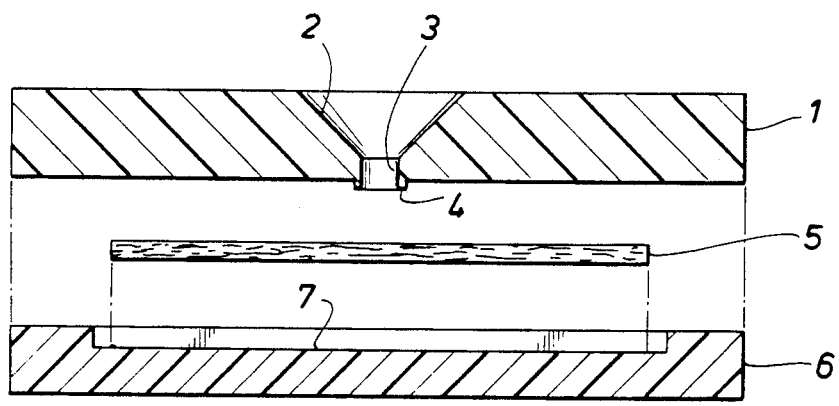

FIG. 2 is a sectional view taken along line 2—2 of FIG. 1 and showing the various parts of the filter in exploded relation.

Figure 3:
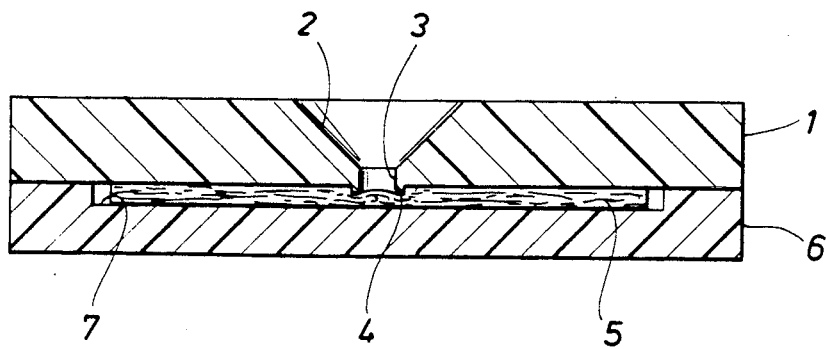

FIG. 3 is a sectional view showing the assembled filter apparatus of FIGS. 1 and 2.

FIG. 4 is a plan view of filter apparatus representing an alternative embodiment of this invention and providing for simultaneous multiple testing of a body fluid sample.

FIG. 5 is a sectional view taken along line 5—5 of FIG. 4 which illustrates one position of the filter apparatus of FIG. 4.

FIG. 6 is a sectional view similar to that of FIG. 5 showing another position of the filter apparatus.

DETAILED DESCRIPTION OF THE INVENTION

This invention relates to compositions useful for staining both gram negative and gram positive bacteria and to various methods of detecting and quantitating bacteria in fluid samples. Broadly stated, the staining apparatus and composition of the invention comprises a filter matrix having a net negative charge, an acid diluent, a dye capable of staining bacteria at basic pH, and a washing reagent which removes the free dye from filter fibers but not from the bacteria. The immobilized bacteria, electrostatically adsorbed to the filter, are readily visible and easily distinguished from free dye which is diffused away from the stained bacteria by the washing reagent.

Since the color intensity of the filter is proportional to the number of bacteria in the fluid sample, quantitative analysis of bacteria may be accomplished by comparing the color intensity of the stained bacteria on the filter surface to a known standard.

The composition and methods of the invention have particular application to the detection and quantitation of bacteria in urine. By means of this invention, rapid and economical detection of urinary tract infection is possible.

More particularly, it has been discovered that dyes soluble at pH 8 to 12 which stain bacteria will do so in the absence of chelating agents. Bacteria are stained by contacting these organisms, which are electrostatically adsorbed to negatively charged filter surfaces, with a protein staining dye at about pH 8 to 12. Any dye capable of staining bacteria which is soluble at about pH 8 to 12 may be employed. However, preferable dyes are Safranin-O or Basic Fuchsin.

It is known that bacterial cells vary in width or diameter with a range of about 0.3 um (microns) to 0.8 um. Filters commonly used in the industry and in prior art for efficient retention of bacteria typically have a pore size of 0.2 unm to 0.45 um. For use in conjunction with the teachings of this invention, a filter having a pore size of 1.0 um to 25 um may be used, depending on the fulid being processed and the presence of other particulates which may effect the flow, diffusion or fluid absorption rate. Such a filter in the pore size range of 1.0 um to 25 um would not be expected to efficiently retain bacterial cells by porosity alone or in the absence of adsorption phenomena.

Bacteria stained in accordance with the present invention may be readily detected if present at a concentration of 50,000 or higher per milliliter, or at lower amounts if concentrated. Stained bacteria which are dispersed in solution will, upon concentration, be readily visible. When concentrated bacteria at sufficient concentration are stained without dispersion, the presence of bacteria is immediately manifest.

Sedimentation and entrapment of bacteria by filtration are examples of effective means for concentrating bacteria. In this current invention, bacteria in urine (their isoelectric charge having been modified by an acid diluent) are adsorbed to a negatively charged filter surface. As the urine-diluent solution diffuses over a wide area, the bacteria therein electrostatically adsorb to the filter at the site where the urine is deposited, providing an effective method for concentrating bacteria. In accordance with the method of this invention, the pores of the filter are not required to be smaller than the bacteria under test.

Filter surfaces which have a net negative charge rather than a net positive charge must be employed. The diluent indicated in this application will reverse the isoelectric charge of negatively charged bacteria, altering the same to a positive charge. Thus, the bacteria in the urine-diluent solution will be immobilized electrostatically by adsorption to the filter matrix whereas free dye, urine pigments and other urinary compounds will diffuse away from the restricted area site of the adsorbed bacteria allowing detection of the stained organisms.

Dye used to stain bacteria at the site of the deposit of the urine-diluent mixture is diffused away from the immobilized stained bacteria adsorbed to the filter. Addition of the washing reagent at the site at which the urine-diluent solution was deposited enhances the diffusion of the free dye from this site without removing the stain from the immobilized bacteria.

Referring now to the drawings, a preferred embodiment of the invention is illustrated in FIG. 1 and consists of a flat, round or square, rigid or semi-rigid disk 1. This disk may be machined, molded or thermoformed from a variety of materials, e.g., polystyrene. The disk preferably measures about one to four inches in diameter or width and features a conical or round depression or reservoir 2 at or near the center of the disk. Located at the bottom of the reservoir the disk defines a short bore forming a small diameter hole or orifice 3 which extends through the entire thickness of the disk. The orifice diameter may be in the range of from about 0.06 inch to about about 0.25 inch.

Though it is not an absolute requirement for performance of the procedure, the disk may feature an orifice lip 4 protruding from the lower surface around the orifice. This orifice lip allows for more efficient flow of fluids into a precise location on the filter paper pad and serves to inhibit the spreading of fluid on the upper surface of the filter pad. The filter pad 5 is positioned adjacent to the lower surface of the disk so that the filter pad is in contact with the orifice or orifice lip. The filter pad may be composed of cellulose, fiberglass or other suitable filter material and exhibits a net negative electrostatic charge.

The position of the filter pad is maintained by "sandwiching" the pad between the disk and a lower filter retainer plate 6. The lower plate may be machined, molded or thermoformed, and features a square or round depression 7 slightly larger in size than the filter pad. The lower plate may be attached to the disk to secure the filter pad in place. This attachment may be by any suitable means such as by an adhesive, solvent welding, or sonic welding. Alternatively, the disk and lower plate may be designed to hinge, snap or screw together to house the filter pad.

In another embodiment of the invention, as evidenced by FIGS. 4–6, an adhesive label or tape 8 is applied to the lower surface 9 of the disk or plate 10 to secure the filter pad, thus eliminating the need for a lower filter retainer plate.

The embodiments described above are useful as a single use disposable, portable unit for detection of bacteria and have particular application for detection of bacteria in fluids, e.g., urine, in situations where conventional methods for bacteria detection are cumbersome or unfeasible, e.g., over-the-counter for consumer home use, physicians' offices, screening clinics, etc.

The disk may be formed to define a reaction well 11 which extends transversely from the tapered reservoir as illustrated in FIG. 4. When the device is placed in a vertical position, with its base 12 resting on any flat horizontal surface the reaction well 11 is positioned to accept and retain sample fluid. When the device is subsequently placed in a horizontal or near horizontal position by 90 degrees clockwise rotation from the position shown in FIG. 4 as evidenced by FIG. 6, the fluid flows out of the reaction well and into the reservoir. The fluid then travels through the orifice and upon contact with the filter pad, is absorbed into the pad. This feature is especially useful in tests requiring incubation or reaction of a bacterial suspension with a chemical substance prior to performance of the bacterial quantitatio test. In particular, a test for determination of antibiotic susceptibility may be performed by incubating a bacterial suspension with an appropriate antibiotic for a period of time during which, if the organism is resistant to the antibiotic, growth of the organism will occur. After the incubation period, the device is placed in a horizontal position to allow the antibiotic-treated bacterial suspension to flow to the reservoir and filter pad, thus allowing for quantitation with the staining composition of the current invention.

A disposable multiple test device is illustrated in FIG. 4 which may be made by molding or thermoforming a device featuring two or more units of the embodiments described above in connection with FIG. 4. This multiple test device has particular application in a test for determination of antibiotic susceptibility. The appropriate antibiotics may be pre-loaded into the reaction well thus allowing for simple test set-up and multiple determination of antibiotic susceptibility.

Although specific embodiments of the invention have been shown and described, it is understood that other embodiments adaptations and modifications may be utilized without departing from the true spirit and scope of the invention. The embodiments, composition and methods described herein may be similarly applied to the staining and detection of bacteria in other fluids, such as culture media, blood, spinal fluids, food washings, milk and water, as well as to staining bacteria from such fluids which have been deposited on filter surfaces.

The minimum quantity of bacteria which can be detected by this staining procedure varies somewhat with the condition and growth phase of the bacterial culture. In general, actively growing, viable bacteria are strongly detected at levels of about 100,000/ml. Non-viable organisms, or organisms in lag phase stain less intensely and thus higher levels of bacteria are required for detection.

The following examples are illustrative of the invention and are not to be taken in a limiting sense.

EXAMPLE 1

Two drops of urine (using a conventional dropping pipette) from a known positive bacteriuric patient was added to 8 drops of acid diluent, pH 1.5 HCl in a test tube. Four drops of the mixture was added to the center of a negatively charged filter. Three drops of Safranin-O dye at 1:1000 in pH 10 carbonate-borate-hydroxyl buffer was added to the filter surface at the site of inoculation of the urine-diluent mixture. Three drops of washing reagent, pH 2.5 HCl was added to the same site to allow diffusion of free dye away from the site of inoculation. Three additional drops of washing reagent was used as a second rinse. The results manifested a 3-4 mm diameter intensely stained filter surface at the site of inoculation with a peripheral ring of free dye about 25 mm from the site of the stained bacteria. Such a result is indicative of a positive bacteriuria test. Comparison of the intensity of the color of the stained bacteria to a known amount of bacteria added to urine indicated about 1,000,000 bacteria per ml urine. Plating of the sample on agar culture verified these results.

EXAMPLE 2

Two drops of urine (using a conventional dropping pipette) from a healthy volunteer (free of urinary-tract infection by conventional assay) was added to eight drops of acid diluent, pH 1.5 HCl in a test tube. Four drops of the mixture was added to the center of a negatively charged filter. The remainder of this experiment was conducted exactly as described in Example 1 above. Upon observation, the filter surface at the site at which the urine-diluent solution was deposited was completely white and the free dye ringed the filter at about 25 mm from the site of the inoculation. Such a result is indicative of a negative bacteriuria test. This result was verified by plating of the sample on agar culture media.

EXAMPLE 3

Employing the procedure set forth in Examples 1 and 2, and the preferred embodiment illustrated in FIG. 1, experiments were conducted with a variety of organisms using Safranin-O as a model dye at pH 10 in carbonate-borate-hydroxyl buffer. The results were as follows:

| Test Organisms 100,000 Bacteria/ml | Intensity of Stain* On Filter Surface |
| --- | --- |
| Normal urine, no bacteria | 0 |
| E. coli | + + |
| S. aureus | + + |
| Proteus vulgaris | + + |
| Pseudomonas | + + |
| Group A Strep. | + + |
| Group D Strep. | + + |
| Klebsiella pn. | + + |

*Site of inoculation of sample of urine-diluent onto the filter surface. Scoring of color intensity: 0 = white, no color;
+ = light pink; + + = pink; + + + = red; + + + + = dark red or magenta.

EXAMPLE 4

Employing the procedures set forth in Examples 1 and 2, and the preferred embodiment illustrated in FIG. 1, experiments were conducted adding different final concentrations of bacteria/ml to normal urine, and proceeding to test 4 drops of the urine-diluent mixture with results as follows. The scoring of filter color intensity is described in Example 3.

| E. coli CFU/ml Added to Normal Urine | Color Intensity Of Filter Surface |
| --- | --- |
| 0 | 0 |
| 10,000 | 0 |

-continued

| E. coli CFU/ml Added to Normal Urine | Color Intensity Of Filter Surface |
| --- | --- |
| 50,000 | + |
| 100,000 | + + |
| 1,000,000 | + + + |
| 10,000,000 | + + + + |

EXAMPLE 5

A test for determination of antibiotic susceptibility may be performed as follows: The multiple test device illustrated in FIG. 4 is placed in a vertical position. Antibiotic solutions (one drop each) are dispensed into reaction wells #1 through #8. One drop of formalin solution is dispensed into well #9 and one drop of distilled water is placed into well #10. A broth suspension of bacteria is diluted to yield approximately 100,000 bacteria/ml, and one drop of this dilution is added to each reaction well #1 through #10. The device is then incubated for three to four hours at 37 degrees C. After the incubation period, 4 drops of pH 1.5 HCl diluent are added to each reaction well. The device is placed in a horizontal position to allow travel of the fluid from the reaction well into the reservoir. After the fluid is absorbed into the filter pad, the dye solution and washing reagent are placed on each filter site as described in Examples 1 and 2 above. After completion of the staining process, the filter pad is visually examined for color development. Formalin treated site #9 manifests a pink (+ +) color and represents the zero-hour control. Site #10 manifests a dark red (+ + + +) color and represents the uninhibited growth control. The color intensity of each site #1 through #8 is compared to the controls for interpretation of antimicrobial susoeptibility. Color intensity equal to or greater than the growth control indicates that the organism is resistant to the antibiotic under test. Color intensity equal to or less than the zero-hour control indicates that the organism is susceptible to the antibiotic.

What is claimed is:

1. A process for concentrating immobilizing and staining bacteria contained within a fluid sample which bacteria normally possesses a net negative charge, comprising:
   (a) diluting a sample fluid with an inorganic acid having a pH in the range of from 1 to 3 to convert said negatively charged bacteria to a net positive charge;
   (b) electrostatically adsorbing said converted net positively charged bacteria in a fluid sample to a designated portion of a net negatively charged filter having a pore size exceeding the size of said bacteria for electrostatic adsorption of net positively charged bacteria to the fibers of said net negatively charged filter;
   (c) staining said adsorbed bacteria with a staining dye operative at a basic pH; and
   (d) diffusing free staining dye from said stained electrostatically adsorbed bacteria to a region of said filter beyond said designated portion, leaving stained bacteria in said designated region for comparative quantitative analysis.

2. The process of claim 1, wherein said inorganic acid is selected from the group consisting of hydrochloric acid, nitric acid and sulfuric acid.

3. The process of claim 1, wherein said staining dye is selected from the group consisting of safranin-O and basic fuchsin.

4. The process of claim 1, wherein said staining dye is a bacteria staining dye operative in a pH range of from about 8 to 12 and soluble in buffers at said pH range.

5. A prcess of claim 1, wherien said staining dye is in a concentration range of from about 0.1% to about 0.001% in a borate-carbonate-hydroxyl buffer at a pH range of from about 8 to about 12.

6. A prcess of claim 5, wherein said staining dye is solubilized in potassium borate, potassium carbonate and potassium hydroxide buffer at a pH range of from about 8 to about 12.

7. A prcess of claim 1, wherein said diffusing is accomplished by washing said stained adsorbed bacteria with a washing reagent composed of an inorganic acid in a pH range of from about 2 to about 4.

8. The process of claim 4, wherein said inorganic acid is selected from the group consisting of hydrochloric acid, nitric acid and sulfuric acid.

9. The process of claim 1, wherein said filter is composed of a material selected from the group consisting of fiberglass and cellulose.

10. The process of claim 1, wherein said fluid sample is urine, and
    the composition of the urine acid mixture being in the range of from about 4 parts of diluent to about 1 part urine.

11. The process of claim 1, wherein said electrostatically adsorbing comprises:
    (a) depositing said fluid-diluent mixture onto the surface of said filter;
    (b) allowing bacteria cells in said fluid sample to adsorb onto the fibers of said filter; and
    (c) allowing said fluid sample to absorb and diffuse into said filter.

12. The process of claim 1, wherein said staining comprises adding staining dye onto said designated portion of said filter surface onto which said diluted fluid sample was initially deposited.

13. The process of claim 12 wherein said staining dye is in a concentration range of from about 0.1% to about 0.001% in a borate-carbonate-hydroxyl buffer at a pH range of from about 8 to about 12.

14. The process of claim 13, wherein said staining dye is solubilized in potassium borate, potassium carbonate and potassium hydroxide buffer at a pH range of from about 8 to about 12.

15. A process as recited in claim 1, wherein said fluid sample is composed of urine and said diffusing comprises:
    adding a washing reagent composed of an inorganic acid in the pH range of from about 2 to about 4 and selected from the group hydrochloric acid, nitric acid and sulfuric acid onto said designated portion of said filter so that the concentrated and stained bacteria are manifest at said designated portion of said filter surface and any free dye deposited at said designated portion of said filter surface with said stained bacteria is diffused from said designated portion of said filter surface in the form of a ring of free dye in the range of from about 10 mm to about 30 mm from the concentrated stained bacteria at said designated portion of said filter surface.

16. A process as recited in claim 1, wherein said stained and adsorbed bacteria is quantitated by comparing the color intensity of said stained bacteria on said filter to a color guide having colors representing the results of tests from samples having known concentrations of bacteria.

17. Apparatus for concentrating, immobilizing and staining bacteria which have been converted to a net positive charge from fluid samples, comprising:
(a) disk means forming upper and lower surfaces and forming an orifice intersecting said lower surface, said disk means further forming sample reservoir means extending from said upper surface and opening through said orifice for conducting a fluid sample to said lower surface;
(b) filter means having a pore size greater than the size of said bacteria for ease of passage of a bacteria containing sample therethrough and having a net negative electrostatic charge for electrostatically adsorbing said net positively charged bacteria to the net negatively charged surfaces thereof; and
(c) retainer means retaining said filter means against said lower surface, a designated portion of said filter means being exposed to said sample reservoir means at said orifice, said filter means extending radially from said opening a sufficient distance permitting radial diffusion of free dye from said designated filter portion exposed at said orifice to thus leave concentrated and stained bacteria from said fluid sample electrostatically adsorbed to said net negatively charged fibers of said filter means at said exposed designated portion of said filter means for color comparison indicating quantitation of said stained bacteria.

18. The apparatus of claim 17, wherein said sample reservoir is of upwardly diverging form extedning from said orifice to said upper surface of said disk means and defines a sufficient volume for receiving a predetermined volume of said fluid sample.

19. The apparatus of claim 17, wherein said retaining means comprises:
(a) plate means forming a filter receptacle of sufficient dimension to receive said filter means therein, said plate means securing said filter means against said lower surface of said disk means; and
(b) means retaining said plate means and said filter means in intimate assembly with said disk means.

20. The apparatus of claim 19, wehrein said disk means defines a peripheral lip projection extending from said disk means toward said filter means and being located about said orifice, said peripheral lip projection engaging said filter means and permitting said radial diffusion of free dye to the portion of means said filter radially outwardly of said peripheral lip projection.

21. The apparatus of claim 17, wherein:
said disk means has reaction well means oriented to retain specimen fluid when said disk means is oriented other than horizontally, said reaction well means communicating said fluid sample to said sample reservoir when said disk means is oriented horizontally; thus permitting reaction of said fluid sample in said reaction well means prior to deposit of said fluid sample from said reaction well means into said sample reservoir means.

22. The apparatus of claim 21, wherien said disk means has a base at one side of said disc means and oriented in transverse realtion to the longitudinal axis of said reaction well means, with said disk positioned by said base said reaction well means is oritned in fluid retaining position thus causing sample fluid to be retained within said reaction well means, upon substantially horizontal positioning of said disk means sample fluid gravitating from said reaction well means into said sample reservoir means.

23. The apparatus of claim 21, wherein said disk means defines a peripheral lip projection about said orifice at the intersection of said orifice and said lower surface, said peripheral lip projection engaging said filter means.

24. The apparatus of claim 23, wherein:
(a) said disk means defines a plurality of spaced sample reservoirs and a plurality of reaction wells each communicating with respective sample reservoirs; and
(b) said disk means defines base means orienting said disk means such that fluid samples in said plurality of reaction wells is prevented from entering said sample reservoirs, upon substantially horizontal positioning of said disk means said fluid samples gravitating from said reaction wells into respective sample reservoirs.

25. The apparatus of claim 17, wherein each retaining means comprises a layer of material covering said filter means and having adhesive peripheral portions thereon, said adhesive peripheral portions having adhesive contact with said lower surface and retaining said filter means in encapsulated assembly with said disk means.

* * * * *